United States Patent
Voelker et al.

(10) Patent No.: US 9,617,567 B2
(45) Date of Patent: Apr. 11, 2017

(54) USE OF SUCROSE AS SUBSTRATE FOR FERMENTATIVE PRODUCTION OF 1,2-PROPANEDIOL

(71) Applicant: METABOLIC EXPLORER, Saint Beauzire (FR)

(72) Inventors: Francois Voelker, Montrond les Bains (FR); Rainer Figge, Le Crest (FR); Philippe Soucaille, Deyme (FR)

(73) Assignee: METABOLIC EXPLORER, Saint Beauzire (FR)

(*) Notice: Subject to any disclaimer, the term of this patent is extended or adjusted under 35 U.S.C. 154(b) by 0 days.

(21) Appl. No.: 14/620,492

(22) Filed: Feb. 12, 2015

(65) Prior Publication Data
US 2015/0159181 A1 Jun. 11, 2015

Related U.S. Application Data

(62) Division of application No. 13/127,642, filed as application No. PCT/EP2008/065131 on Nov. 7, 2008, now abandoned.

(51) Int. Cl.
C12P 7/18 (2006.01)
(52) U.S. Cl.
CPC .................. C12P 7/18 (2013.01)
(58) Field of Classification Search
None
See application file for complete search history.

(56) References Cited

U.S. PATENT DOCUMENTS

| 6,087,140 A | 7/2000 | Cameron et al. |
| 2007/0072279 A1 | 3/2007 | Meynial-Salles et al. |
| 2010/0261239 A1 | 10/2010 | Soucaille et al. |
| 2010/0285547 A1 | 11/2010 | Soucaille et al. |

FOREIGN PATENT DOCUMENTS

| EP | 1149911 A2 | 10/2001 |
| EP | 1318196 A1 | 6/2003 |
| WO | WO 98/37204 A1 | 8/1998 |
| WO | WO 99/28481 A1 | 6/1999 |
| WO | WO 2004/087936 A1 | 10/2004 |
| WO | WO 2005/073364 A2 | 8/2005 |
| WO | WO 2008/116848 A1 | 10/2008 |
| WO | WO 2008/116852 A1 | 10/2008 |
| WO | WO 2008/116853 A1 | 10/2008 |

OTHER PUBLICATIONS

Bockmann et al., "Characterization of a chromosomally encoded, non-PTS metabolic pathway for sucrose utilization in *Escherichia coli* EC3132," Mol Gen Genet 235:22-32, 1992.*
Altaras et al., "Conversion of Sugars to 1,2-Propanediol by Thermoanaerobacterium thermosaccharolyticum HG-8," Biotechnol. Prog., vol. 17, No. 1, 2001 (Published on Web: Dec. 5, 2000), pp. 52-56.
Altaras et al., "Enhanced Production of (R)-1,2-Propanediol by Metabolically Engineered *Escherichia coli*," Biotechnol. Prog., vol. 16, No. 6, 2000 (Published on Web: Aug. 25, 2000), pp. 940-946.
Altaras et al., "Metabolic Engineering of a 1,2-Propanediol Pathway in *Escherichia coli*," Applied and Environmental Microbiology, vol. 65, No. 3, Mar. 1999, pp. 1180-1185, XP-002293970.
Anderson, "Growth Requirements of Virus-Resistant Mutants of *Escherichia Coli* Strain "B"," Proc. Natl. Acad. Sci., vol. 32, 1946 (Communicated Mar. 21, 1946), pp. 120-128.
Badía et at., "Fermentation Mechanism of Fucose and Rhamnose in *Salmonella typhimurium* and Klebsiella pneumoniae," Journal of Bacteriology, vol. 161, No. 1, Jan. 1985, pp. 435-437.
Bekers et al., "Sugar Beet Diffusion Juice and Syrup as Media for Ethanol and Levan Production by Zymomonas mobilis," Food Biotechnology, vol. 13, No. 1, 1999, pp. 107-119.
Berríos-Rivera et al., "The effect of carbon sources and lactate dehydrogenase deletion on 1,2-propanediol production in *Escherichia coli*," J. Ind. Microbiol. Biotechnol., vol. 30, 2003, pp. 34-40.
Calabia et at., "Production of $_D$-lactic acid from sugarcane molasses, sugarcane juice and sugar beet juice by Lactobacillus delbrueckii," Biotechnol. Lett., vol. 29, 2007 (Published online: May 31, 2007), pp. 1329-1332.
Cameron et al., "A Novel Fermentation: The Production of R(-)-1,2-Propanediol and Acetol by Clostridium Thermosaccharolyticum," Nature Bio/Technology, vol. 4, Jul. 1986, pp. 651-654, XP-002067773.
Cameron et al., "Metabolic Engineering of Propanediol Pathways," Biotechnol. Prog., vol. 14, No. 1, 1998 (Published on Web: Jan. 16, 1998), pp. 116-125, XP002939239.
Huang et al., "Characterization of Methylglyoxal Synthase from Clostridium acetobutylicum ATCC 824 and Its Use in the Formation of 1,2-Propanediol," Applied and Environmental Microbiology, vol. 65, No. 7, Jul. 1999, pp. 3244-3247.
International Search Report and Written Opinion of the International Searching Authority (Forms PCT/ISA/210 and PCT/ISA/237), dated Aug. 12, 2009, for International Application No. PCT/EP2008/065131.
Jahreis et al., "Adaptation of Sucrose Metabolism in the *Escherichia coli* Wild-Type Strain EC3132," Journal of Bacteriology, vol. 184, No. 19, Oct. 2002, pp. 5307-5316.

(Continued)

*Primary Examiner* — Rosanne Kosson
(74) *Attorney, Agent, or Firm* — Birch, Stewart, Kolasch & Birch, LLP

(57) ABSTRACT

The present invention is relative to a method for producing 1,2-propanediol by fermentation, comprising: cultivating a microorganism producing 1,2-propanediol in an appropriate medium comprising a source of sucrose, and recovering the 1,2-propanediol being produced, wherein the microorganism is able to utilize sucrose as sole carbon source for the production of 1,2-propanediol. In a preferred aspect of the invention, the source of sucrose is obtained from plant biomass, and is in particular sugar cane juice.

16 Claims, No Drawings

(56) References Cited

OTHER PUBLICATIONS

Monot et al., "Acetone and Butanol Production by Clostridium acetobutylicum in a Synthetic Medium," Applied and Environmental Microbiology, vol. 44, No. 6, Dec. 1982, pp. 1318-1324.

Penfold et al., "Increased hydrogen production by *Escherichia coli* strain HD701 in comparison with the wild-type parent strain MC4100," Enzyme and Microbial Technology, vol. 33, 2003, pp. 185-189.

Penfold et al., "Production of $H_2$ from sucrose by *Escherichia coli* strains carrying the pUR400 plasmid, which encodes invertase activity," Biotechnology Letters, vol. 26, 2004, pp. 1879-1883.

Peters, "Carbohydrates for fermentation," Biotechnology Journal, vol. 1, 2006, pp. 806-814.

Sánchez-Riera et al., "Influence of Environmental Factors in the Production of R(-)-1,2-Propanediol by Clostridium Thermosaccharolyticum," Biotechnology Letters, vol. 9, No. 7, 1987, pp. 449-454.

Schaefer et al., "Automated Sampling Device for Monitoring Intracellular Metabolite Dynamics," Analytical Biochemistry, vol. 270, 1999, pp. 88-96.

Schmid et al., "Plasmid-mediated sucrose metabolism in *Escherichia coli* K12: mapping of the scr genes of pUR400," Molecular Microbiology, vol. 2, No. 1, 1988, pp. 1-8.

Schmid et al., "Plasmid-Mediated Uptake and Metabolism of Sucrose by *Escherichia coli* K-12," Journal of Bacteriology, vol. 151, No. 1, Jul. 1982, pp. 68-76.

Shukla et al., "Production of $_D$(-)-lactate from sucrose and molasses," Biotechnology Letters, vol. 26, 2004, pp. 689-693.

Soucaille et al., "Program: Metabolic Engineering VII: Health and Sustainability," Session A Posters, ECI—Engineering Conferences International, Sep. 14-19, 2008, Puerto Vallarta, Mexico, pp. 1-19, XP-002537942.

Tran-Din et al., "Formation of $_D$(-)-1,2-propanediol and $_D$(-)-lactate from glucose by Clostridium sphenoides under phosphate limitation," Archives of Microbiology, vol. 142, 1985, pp. 87-92.

Tsunekawa et al., "Acquisition of a Sucrose Utilization System in *Escherichia coli* K-12 Derivatives and Its Application to Industry," Applied and Environmental Microbiology, vol. 58, No. 6, Jun. 1992, pp. 2081-2088.

Vasconcelos et al., "Regulation of Carbon and Electron Flow in Clostridium acetobutylicum Grown in Chemostat Culture at Neutral pH on Mixtures of Glucose and Glycerol," Journal of Bacteriology, vol. 176, No. 3, Mar. 1994, pp. 1443-1450.

Voelker et al., "2008 Exhibitors and Schedule," The Society for Industrial Microbiology (SIM), 2008 Annual Meeting, Aug. 10-12, 2008, San Diego, USA, pp. 23 and 40, XP-002537943.

Wiesenborn et al., "Thiolase from Clostridium acetobutylicum ATCC 824 and Its Role in the Synthesis of Acids and Solvents," Applied and Environmental Microbiology, vol. 54, No. 11, Nov. 1988, pp. 2717-2722.

\* cited by examiner

USE OF SUCROSE AS SUBSTRATE FOR FERMENTATIVE PRODUCTION OF 1,2-PROPANEDIOL

CROSS REFERENCE TO RELATED APPLICATIONS

This application is a divisional application of U.S. application Ser. No. 13/127,642, filed May 4, 2011, which is a §371 National Stage Application of PCT/EP2008/065131, filed Nov. 7, 2008, the contents of which are incorporated herein by reference in their entireties.

BACKGROUND OF THE INVENTION

Field of the Invention

The present invention relates to fermentation processes, to microorganisms and to substrates useful for fermentation. In particular, this invention is related to the production of 1,2-propanediol by fermentation, from a sucrose-containing medium, in particular from plant biomass.

Description of Related Art 1,2-propanediol or propylene glycol, a C3 dialcohol, is a widely-used chemical. It is a component of unsaturated polyester resins, liquid detergents, coolants, anti-freeze and de-icing fluids for aircraft. Propylene glycol has been increasingly used since 1993-1994 as a replacement for ethylene derivatives, which are recognised as being more toxic than propylene derivatives.

1,2-propanediol is currently produced by chemical means using a propylene oxide hydration process that consumes large amounts of water. Propylene oxide can be produced by either of two processes, one using epichlorhydrin, and the other hydroperoxide. Both routes use highly toxic substances. In addition, the hydroperoxide route generates by-products such as tert-butanol and I-phenyl ethanol. For the production of propylene to be profitable, a use must be found for these by-products. The chemical route generally produces racemic 1,2-propanediol, whereas each of the two stereoisomers (R)1,2-propanediol and (S)1,2-propanediol are of interest for certain applications (e.g. chiral starting materials for specialty chemicals and pharmaceutical products).

The disadvantages of the chemical processes for the production of 1,2-propanediol make biological synthesis an attractive alternative. Two routes have been characterized for the natural production of 1,2-propanediol from sugars by microorganisms. In the first route 6-deoxy sugars (e.g. L-rhamnose or L-fucose) are cleaved into dihydroxyacetone phosphate and (S)-lactaldehyde, which can be further reduced to (S)-1,2-propanediol (Badia et al, 1985). This route is functional in *E. coli*, but cannot yield an economically feasible process due to the elevated cost of the deoxyhexoses. The second route is the metabolism of common sugars (e.g. glucose or xylose) through the glycolysis pathway followed by the methylglyoxal pathway. Dihydroxyacetone phosphate is converted to methylglyoxal that can be reduced either to lactaldehyde or to acetol. These two compounds can then undergo a second reduction reaction yielding 1,2-propanediol. This route is used by natural producers of (R)-1,2-propanediol, such as *Clostridium sphenoides* and *Thermoanaerobacter thermosaccharolyticum*. These two organisms have been used to produce 1,2-propanediol from different sugars, namely monosaccharides (D-glucose, D-mannose, D-galactose for the hexoses and D-xylose or L-arabinose for the pentoses) or disaccharides (lactose or cellobiose) or mixtures (Tran Din and Gottschalk, 1985, Cameron and Cooney, 1986, Sanchez-Rivera et al, 1987, Altaras et al, 2001). The best performance obtained was a titer of 9 g/l and a yield from glucose of 0.2 g/g (Sanchez-Rivera et al, 1987). However, the improvement of the performances obtained with these organisms is likely to be limited due to the shortage of available genetic tools. The same synthesis pathway is functional in *E. coli* or other *Entcrobacteriaccac* and several investigations have been done by the group of Cameron (Cameron et al, 1998, Altaras and Cameron, 1999, Altaras and Cameron, 2000) and the group of Bennett (Huang et al, 1999, Berrios-Rivera et al, 2003) for the production of 1,2-propanediol in this organism with carbon sources limited to D-glucose or D-fructose. The best result obtained in an anaerobic fed-batch fermenter was a production of 4.5 g/l 1,2-propanediol with a yield of 0.19 g/g from glucose (Altaras and Cameron, 2000). Results obtained with the same approach but with lower titers and yields are also described in the patent WO 98/37204, although using different carbon sources, namely galactose, lactose, sucrose and xylose but also glucose. The titers obtained with disaccharides (lactose and sucrose) were very low (6 mg/l and 7 mg/l respectively). Better production results were described with a rationally designed then evolved E. coli strain in patent application WO 2005/073364. A 1,2-propanediol titer of 1.8 g/l was obtained, with a yield of 0.35 g/g of glucose consumed. Production of 1,2-propanediol and hydroxyacetone was also described using recombinant yeast in patent WO 99/28481.

Carbon sources used in fermentation media generally consisted in carbohydrates, mostly derived from plants. Sucrose is obtained from sugar plants such as sugar beet, sugarcane, sweet sorghum, sugar maple, sugar palms or blue agaves. Starch is the most abundant storage carbohydrate in plants. The most important starch sources are cereals (corn, wheat, rice), manioc, sweet potatoes and potatoes. Starch is not metabolized by most microorganisms but can be processed to fermentable feedstocks by the starch industry. Inulin or inulin-like polymers (mainly consisting of fructose units) are the second most abundant storage carbohydrate in plants and are found in chicory, Jerusalem artichoke or dahlia. Lignocellulosic biomass composed of cellulose, hemicellulose and lignin is also a promising source of carbohydrate but still under development (Peters, 2006). As the cost of the biotechnologically produced commodity chemicals are mainly related to the cost of raw material (i.e. the cost of the fermentation substrate), use of refined sugars such as glucose or sucrose is not an economically sustainable choice for industrial scale production. Less expensive substrates are needed that retain a high content of fermentable sugar. In this respect, sucrose containing carbon sources coming from the sugar industry represent a good option.

Sucrose is produced from sugar beet containing 16 to 24% sucrose by sugar beet processing in several steps. The cleaned and washed beets are sliced into long strips called cossettes that are extracted with hot water by diffusion to get a sucrose juice called raw juice and containing 10 to 15% sucrose. The second step is the purification of the raw juice by alkalization and carbonation using lime and then carbon dioxide to remove the impurities and get the thin juice. The evaporation process increases the sucrose concentration in the thin juice by removing water to get the thick juice with a sucrose content of 50 to 65%. This concentrated sucrose juice is then crystallised and the crystals are separated by centrifugation and then washed and dried to get pure sugar. One or more crystallisation steps can be applied to get sucrose of various purity grades. By-products of sugar beet processing include pulp (the exhausted cossettes) and molasses (the remaining mother-liquor from the crystallisation having still a sucrose content of 40 to 60%).

Sucrose is also produced from sugar cane (7 to 20% sucrose content) by the sugar industry. The harvested sugar cane is cleaned before the milling process for extraction of the juice. The structure of the cane is broken and then grinded and at the same time the sucrose is extracted with water to get the raw juice. The crushed cane exhausted from sugar is called bagasse. This residue is primarily used as fuel source to generate process steam. The raw juice is then clarified by adding lime and heating and the clarified juice is separated from the precipitate. The lasts steps of the process, evaporation to get a concentrated syrup and crystallisation are essentially the same as for the sugar beet processing. The by-products of sugarcane processing include bagasse, filter cake from clarification of raw juice and different kind of molasses, still containing significant amount of sucrose.

The different sucrose containing intermediates, products or by-products from the sugar processes (raw juice, thin or clarified juice, thick juice, sucrose syrup, pure sucrose, molasses) may serve as fermentation feedstock. For example, the sugar industry in Brazil is using the clarified sugarcane juice for ethanol production in order to use it as a substitute to gasoline. Recent examples in literature using crude sucrose containing products include ethanol production from sugar beet diffusion juice by *Zymomonas mobilis* (Beckers et al., 1999), production of D-lactate from molasses by *E. coli* (Shukla et al., 2004) and production of D-lactate from sugarcane molasses, sugarcane juice or sugar beet juice by *Lactobacillus delbrueckii* (Calabia et al., 2007).

Two different systems have been characterized for the uptake and utilization of sucrose in sucrose-positive bacteria (i.e. bacteria able to utilize sucrose)

The first one is based on a phosphoenol pyruvate (PEP)-dependent sucrose phosphotransferase system (sucrose PTS) where sucrose is taken up and phosphorylated using phosphoenol pyruvate (PEP) as a donor to yield intracellular sucrose-6-phosphate. Sucrose-6-phosphate is then hydrolysed to D-glucose-6-phosphate and D-fructose by an invertase. D-fructose is further phosphorylated to D-fructose-6-phosphate by an ATP-dependent fructokinase and can then enter the central metabolism. Such a system has been described in several bacterial species, gram-positive as well as gram-negative. Among Entcrobacteriaccac, more than 90% of wild-type *Klebsiella* but less than 50% of *Escherichia* and less than 10% of *Salmonella* strains are sucrose positive.

A conjugative plasmid pUR400 bearing the genes scrKYABR coding for the sucrose PTS has been isolated from *Salmonella* (Schmid et al., 1982, Schmid et al., 1988).

A second non-PTS system was discovered more recently in *E. coli* EC3132 (Bockmann et al., 1992). This system involve the genes cscBKAR coding for a sucrose:proton symport transport system (CscB), a fructokinase (CscK), an invertase (CscA) and a sucrose-specific repressor (CscR).

*Escherichia coli* K12 and its derivatives (including MG1655) cannot utilize sucrose. However, this ability can be conferred by the transfer of the genes coding for the two previously described systems. This has been demonstrated by transferring the plasmid pUR400 in *E. coli* K12 (Schmid et al, 1982) or different plasmids (including pKJL101-1) bearing the cscBKAR genes in a sucrose negative strain of *E. coli* (Jahreis et al., 2002). As for industrial application, tryptophan production from sucrose has been documented in *E. coli* K12 (Tsunekawa et al., 1992), hydrogen production was shown in *E. coli* carrying the pUR400 plasmid (Penfold and Macaskie, 2004) and production of different amino-acids by transferring both systems, PTS and non-PTS was reported in patent application EP1149911.

Production of 1,2-propanediol from sucrose is mentioned in *Clostridium thermosaccharolyticum* (later renamed *T. thermosaccharolyticum*) by Cameron and Cooney (1986) but only traces were recorded whereas amount higher than 3 g/l with yields higher than 0.1 g/g substrate were obtained with other carbon sources.

Production of 1,2-propanediol from sucrose is also mentioned in patent application WO98/37204. However, the strain *E. coli* AA200 transformed with the plasmid pSEARX produces only 7 mg/l of 1,2-propanediol from 10 g/l of sucrose, whereas the same microorganism produces from 49 to 71 mg/l of 1,2-propanediol from monosaccharides. These very low figures of production cast doubt about the true ability of these organisms to produce 1,2-propanediol from sucrose. In our opinion, the strain AA200, which is derived from *E. coli* K12, should not have the ability to import and then metabolize sucrose.

These previous reports clearly indicated to the man skilled in the art that the use of sucrose to produce 1,2-propanediol was not a good option.

Surprisingly, by introducing different systems for sucrose utilization in *E. coli* strains unable to utilize sucrose, the inventors of the present invention were able to obtain improved yield for 1,2-propanediol production from sucrose.

Furthermore, the inventors demonstrated that any sucrose-containing medium, such as a juice or molasses from a plant feedstock, could be used as a substrate for the fermentative production of 1,2-propanediol.

SUMMARY OF THE INVENTION

The present invention is relative to a method for producing 1,2-propanediol by fermentation, comprising:
cultivating a microorganism producing 1,2-propanediol in an appropriate medium comprising a source of sucrose, and
recovering the 1,2-propanediol being produced,
wherein the microorganism is able to utilize sucrose as sole carbon source for the production of 1,2-propanediol.

In particular, the invention describes the use of a modified microorganism able to use sucrose as a sole source of carbon, said sucrose being obtained from biomass, in particular from plant biomass.

DETAILED DESCRIPTION OF A PREFERRED EMBODIMENT

As used herein the following terms may be used for interpretation of the claims and specification.

According to the invention the terms 'cultivating', 'culture', 'growth' and 'fermentation' are used interchangeably to denote the growth of bacteria in an appropriate growth medium containing a simple carbon source. Fermentation is a classical process that can be performed under aerobic, microaerobic or anaerobic conditions.

The term 'appropriate medium' according to the invention denotes a medium of known molecular composition adapted to the growth of the micro-organism. In particular, said medium contains at least a source of phosphorus and a source of nitrogen. Said appropriate medium is for example a mineral culture medium of known set composition adapted to the bacteria used, containing at least one carbon source.

Said appropriate medium may also designate any liquid comprising a source of nitrogen and/or a source of phosphorus, said liquid being added and/or mixed to the source of sucrose. In particular, the mineral growth medium for *Enterobacteriaceae* can thus be of identical or similar composition to M9 medium (Anderson, 1946), M63 medium (Miller, 1992) or a medium such as defined by Schaefer et al. (1999), and in particular the minimum culture medium named MML11PG1_100 described below:

TABLE 1 composition of minimal medium MML11PG1_100 with glucose as carbon source.

| Constituent | Concentration (g/l) |
|---|---|
| EDTA | 0.0084 |
| $CoCl_2\ 6H_2O$ | 0.0025 |
| $MnCl_2\ 4H_2O$ | 0.0150 |
| $CuCl_2\ 2H_2O$ | 0.0015 |
| $H_3BO_3$ | 0.0030 |
| $Na_2MoO_4\ 2H_2O$ | 0.0025 |
| $Zn(CH_3COO)_2\ 2H_2O$ | 0.0130 |
| Fe(III) citrate $H_2O$ | 0.1064 |
| Citric acid | 1.70 |
| $KH_2PO_4$ | 1.65 |
| $K_2HPO_4\ 3H_2O$ | 0.92 |
| $(NH_4)_2HPO_4$ | 0.40 |
| $(NH_4)_2SO_4$ | 4.88 |
| $MgSO_4\ 7H_2O$ | 1.00 |
| $CaCl_2\ 2H_2O$ | 0.08 |
| Thiamine | 0.01 |
| Glucose | 20.00 |
| MOPS buffer | 40.00 |

The pH of the medium is adjusted to 6.8 with sodium hydroxide.

The carbon source 'glucose' can be replaced in this medium by any other carbon source, in particular by sucrose or any sucrose-containing carbon source such as sugarcane juice or sugar beet juice.

The growth medium for *Clostridiaceae* can be of identical or similar composition to Clostridial Growth Medium (CGM, Wiesenborn et al., 1987) or a mineral growth medium as given by Monot et al. (1982) or Vasconcelos et al. (1994).

The term 'sucrose' designates a disaccharide of glucose and fructose linked by a α(1,2) glycosidic bond, with the molecular formula $C_{12}H_{22}O_{11}$. Its systematic name is α-D-glucopyranosyl-(1⇆2)-β-D-fructofuranoside.

The term 'sucrose source' or 'source of sucrose' designates any medium, liquid or solid, containing sucrose in different concentrations, in particular from 1 to 100% of sucrose.

The term 'producing 1,2-propanediol' means that the production of the microorganism in the culture broth can be recorded unambiguously by standard analytical means known by those skilled in the art. The limit of quantification of HPLC for 1,2-propanediol, which is the preferred technique used to quantify this compound, is 25 mg/l. Therefore, the term "producing 1,2-propanediol" means according to the invention that the production levels have to be above 25 mg/l.

The term 'able to utilize sucrose as sole carbon source' indicates that the microorganism can grow in a medium containing sucrose as unique carbon source. Therefore, the definition of a "microorganism able to utilize sucrose as sole carbon source for the production of 1,2-propanediol" means that the microorganism, when grown in a medium containing sucrose as sole carbon source, can produce at least 25 mg/l of 1,2-propanediol. It is however understood that in the method for producing 1,2-propanediol according to the invention, the sucrose source in the culture medium can comprise additional carbon sources in addition to sucrose such as hexoses (such as glucose, galactose or lactose), pentoses, monosaccharides, disaccharides (such as sucrose, cellobiose or maltose)), oligosaccharides, starch or its derivatives, hemicelluloses, glycerol and combinations thereof.

According to a preferred aspect of the invention, the microorganism has been genetically modified to be able to utilize sucrose as sole carbon source, for the production of 1,2-propanediol.

In a specific embodiment of the invention, the microorganism comprises functional genes coding for a PTS sucrose utilization system. A PTS sucrose utilization system is a system for sucrose utilization based on the transport of sucrose by a phosphoenolpyruvate (PEP)-dependent sucrose phosphotransferase system (Sucrose-PTS). A phosphotransferase system couples the transport of a sugar (e.g. sucrose or glucose) with the phosphorylation of the sugar using PEP as phosphate donor. After transport into the cell, the sucrose-phosphate is cleaved into glucose-6-phosphate and fructose by an invertase. Fructose is then phosphorylated into fructose-6-phosphate by a fructokinase. The genes coding for this PTS sucrose utilization system can be controlled by a regulatory protein.

In a preferred aspect of the invention, the microorganism expresses naturally or has been modified with the introduction of the genes : scrKYABR (scrK coding for a fructokinase, scrY coding for a porin, scrA coding for the Protein IIBC, scrB coding for a sucrose-6-P invertase, scrR coding for a repressor) from *Salmonella*. A conjugative plasmid pUR400 bearing said genes scrKYABR might be used to transform the microorganism. These genes can be used all together in combination, or in any combination comprising at least one of these genes. In particular, the gene scrR can be omitted.

The designation of these genes has a more general meaning according to the invention, and covers the corresponding genes in other micro-organisms. Using the GenBank references of the genes from *Salmonella*, those skilled in the art can determine equivalent genes in other organisms than *Salmonella*.

The means of identification of the homologous sequences and their percentage homologies are well-known to those skilled in the art, and include in particular the BLAST programmes that can be used on the website http://www.ncbi.nlm.nih.gov/BLAST/ with the default parameters indicated on that website. The sequences obtained can be exploited (aligned) using for example the programmes CLUSTALW (http://www.ebi.ac.uk/clustalw/), with the default parameters indicated on these websites.

The PFAM database (protein families database of alignments and hidden Markov models http://www.sanger.ac.uk/Software/Pfam/) is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins http://www.ncbi.nlm.nih.gov/COG/) are obtained by comparing protein sequences derived from 66 fully sequenced unicellular genomes representing 14 major phylogenetic lines. Each COG is defined from at least three lines, making it possible to identify ancient conserved domains.

Several techniques are currently used by the man skilled in the art for introducing DNA into a bacterial strain. A preferred technique is electroporation, which is well known to those skilled in the art.

In another embodiment of the invention, the microorganism comprises functional genes coding for a non-PTS sucrose utilization system. A non-PTS sucrose utilization system is a system for sucrose utilization based on transport of sucrose by a system independent of phosphoenolpyruvate. After transport into the cell, the sucrose is cleaved into glucose and fructose by an invertase. Fructose is then phosphorylated into fructose-6-phosphate by a fructokinase and glucose is phosphorylated into glucose-6-phosphate by a glucokinase. The genes coding for this non-PTS sucrose utilization system can be controlled by a regulatory protein. In a preferred aspect of the invention, the microorganism expresses naturally or has been modified with the introduction of the genes from *E. coli* EC3132 i.e. the genes cscBKAR coding for a sucrose:proton symport transport system (cscB), a fructokinase (cscK), an invertase (cscA) and a sucrose-specific repressor (cscR). These genes can be used all together in combination or in any combination comprising at least one of these genes. In particular, the gene cscR can be omitted. Homologous genes from other organisms can also be used.

The designation of these genes has a more general meaning according to the invention, and covers the corresponding genes in other micro-organisms. Using the GenBank references of the genes from *E. coli*, those skilled in the art can determine equivalent genes in other organisms than *E. coli* (see above).

In a specific aspect of the invention, the microorganism is characterized by an improved activity of the biosynthesis pathway of 1,2-propanediol. Microorganisms optimized for the production of 1,2-propanediol have been extensively disclosed in patent applications WO 2005/073364, WO 2008/116853, WO 2008/116852 and WO 2008/116848, that are here incorporated as references.

The microorganisms according to the invention are bacteria, yeast or fungi.

Preferentially, the microorganism is selected from the group consisting of *Enterobacteriaceae, Bacillaceae, Clostridiaceae, Streptomycetaceae* and *Corynebacteriaceae*.

More preferentially, the microorganism is selected from the group consisting of *Escherichia coli, Klebsiella pneumoniae, Thermoanaerobacterium thermosaccharolyticum, Clostridium sphenoides* or *Saccharomyces cerevisiae*.

The culture conditions for the fermentation process can be readily defined by those skilled in the art. In particular, bacteria are fermented at temperatures between 20° C. and 55° C., preferably between 25° C. and 40° C., and preferably at about 35° C. for *Clostridiaceae* and at about 37° C. for *Enterobacteriaceae*.

This process can be carried out either in a batch process, in a fed-batch process or in a continuous process. Fermentation is a classical process that can be performed under aerobic, microaerobic or anaerobic conditions.

'Under aerobic conditions' means that oxygen is provided to the culture by dissolving the gas into the liquid phase. This could be obtained by (1) sparging oxygen containing gas (e.g. air) into the liquid phase or (2) shaking the vessel containing the culture medium in order to transfer the oxygen contained in the head space into the liquid phase. Advantages of the fermentation under aerobic conditions instead of anaerobic conditions is that the presence of oxygen as an electron acceptor improves the capacity of the strain to produce more energy in form of ATP for cellular processes. Therefore the strain has its general metabolism improved.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

In a specific aspect of the invention, the sucrose source is obtained from biomass, in particular from plant biomass. The whole plant or any specific part of a plant can be used to prepare the raw material used as sucrose source. The preparation can be based on any treatment known by those skilled in the art to extract sucrose from a sucrose-containing plant biomass.

In a preferred aspect of the invention, the sucrose source is obtained from a plant chosen among the group consisting of : sugarcane, sugar beet, sweet sorghum, sugar maple, sugar palm and blue agave.

The source of sucrose may in particular be obtained from sugarcane or sugar beet.

Different forms of sucrose source can be used according to the invention, such as a juice, a concentrated juice, a syrup, a clarified juice, molasses or crystallized sucrose.

A preferred form is the raw juice from sugar cane, directly extracted from the plant without any treatment. Briefly, the harvested sugar cane is cleaned before the milling process for extraction of the juice. The structure of the cane is broken and then grinded, and at the same time the sucrose is extracted with water to get the raw juice.

The raw juice may then be clarified by adding lime and heating and the clarified juice is separated from the precipitate. Concentrated syrup is obtained by evaporation.

In another embodiment of the invention, the sucrose source may be a final product, an intermediate product or a by-product of the sugarcane or sugar beet industry.

As some crude sucrose sources, particularly those obtained from biomass as mentioned above, contain other nutrients that can be used for growth of microorganisms in addition to the carbon source, an appropriate medium for the growth of microorganisms can be designed either by using the sucrose source alone, i.e. the appropriate medium consists of the source of sucrose, or by complementing the sucrose source with a source of phosphorus and/or a source of nitrogen.

Preferentially, the sucrose source comprises at least 7% of sucrose.

EXAMPLES

Example 1

Construction of Two Strains of *E. coli* Producing 1,2-propanediol and Able to Utilize Sucrose as Sole Carbon Source The *E. coli* strain MG1655 lpd*, ΔtpiA, ΔpflAB, ΔadhE, ΔldhA::Cm, ΔgloA, ΔaldA, ΔaldB, Δedd evolved in chemostat culture under anaerobic conditions and adapted for growth in minimal medium was obtained as described in WO 2008/116852. This strain was named evolved strain *E. coli* MG1655 lpd*, ΔtpiA, ΔpflAB, ΔadhE, ΔldhA::Cm, ΔgloA, ΔaldA, ΔaldB, Δedd.

The chloramphenicol resistance cassette was eliminated in said evolved strain and the presence of the modifications previously built in the strain was checked as previously described in WO 2008/116852.

Two plasmids were used to confer the ability to utilize sucrose to said *E. coli* strain:
  pUR400, bearing the genes coding for the sucrose-PTS system such as described in Schmid et al. (1982)
  pKJL101.1, bearing the genes coding for the sucrose permease and kinase system such as described in Jahreis et al. (2002).

These plasmids were introduced separately into the evolved strain *E. coli* MG1655 lpd*, ΔtpiA, ΔpflAB, ΔadhE, ΔldhA, ΔgloA, ΔaldA, ΔaldB, Δedd by electroporation.

The two strains obtained were named respectively:
  evolved *E. coli* MG1655 lpd*, ΔtpiA, ΔpflAB, ΔadhE, ΔldhA, ΔgloA, ΔaldA, ΔaldB, Δedd (pUR400), and
  evolved *E. coli* MG1655 lpd*, ΔtpiA, ΔpflAB, ΔadhE, ΔldhA, ΔgloA, ΔaldA, ΔaldB, Δedd (pKJL101.1).

Example 2

Production of 1,2-propanediol with Sucrose as Sole Carbon Source

The strains obtained as described in Example 1 and the strain without plasmid used as control were cultivated in an Erlenmeyer flask assay under aerobic conditions in minimal medium MML11PG1_100 (see composition above) with 20 g/l glucose or sucrose as sole carbon source. Glucose as carbon source was used as control.

The culture was carried out at 34° C. and the pH was maintained by buffering the culture medium with MOPS.

At the end of the culture, 1,2-propanediol, and residual glucose or sucrose in the fermentation broth were analysed by HPLC and the yields of 1,2-propanediol over glucose or the yields of 1,2-propanediol over sucrose were calculated.

TABLE 2 production of 1,2-propanediol in minimal medium with glucose or sucrose as carbon source.

| Strain/Carbon source | 1,2-propanediol titer (g/l) | 1,2-propanediol yield (g/g carbon source) |
|---|---|---|
| Evolved *E. coli* MG1655 lpd*, ΔtpiA, ΔpflAB, ΔadhE, ΔldhA, ΔgloA, ΔaldA, ΔaldB, Δedd/sucrose | ND (n = 1) | — (n = 1) |
| Evolved *E. coli* MG1655 lpd*, ΔtpiA, ΔpflAB, ΔadhE, ΔldhA, ΔgloA, ΔaldA, ΔaldB, Δedd (pUR400)/glucose | 3.89 +/− 0.12 (n = 3) | 0.20 +/− 0.01 (n = 3) |
| Evolved *E. coli* MG1655 lpd*, ΔtpiA, ΔpflAB, ΔadhE, ΔldhA, ΔgloA, ΔaldA, ΔaldB, Δedd (pUR400)/sucrose | 2.26 +/− 0.27 (n = 6) | 0.12 +/− 0.01 (n = 6) |
| Evolved *E. coli* MG1655 lpd*, ΔtpiA, ΔpflAB, ΔadhE, ΔldhA, ΔgloA, ΔaldA, ΔaldB, Δedd (pKJL101.1)/glucose | 3.55 +/− 0.21 (n = 3) | 0.19 +/− 0.01 (n = 3) |
| Evolved *E. coli* MG1655 lpd*, ΔtpiA, ΔpflAB, ΔadhE, ΔldhA, ΔgloA, ΔaldA, ΔaldB, Δedd (pKJL101.1)/sucrose | 4.86 +/− 0.77 (n = 6) | 0.26 +/− 0.03 (n = 6) |

ND means 'not detected'.
n is the number of repetitions of the same experiment.
The figures given are the mean and standard deviation of the figures obtained for n repetitions.

Example 3

Production of 1,2-propanediol with Sugarcane Juice as Carbon Source

The strains obtained as described in Example 1 were cultivated in an Erlenmeyer flask assay under aerobic conditions in minimal medium MML11PG1_100 with sugarcane juice (20 g/l sucrose equivalent) as carbon source.

The sugarcane juice used in this experiment was obtained from a sugar mill in the south-east aria area and was collected right after the clarification with lime of the raw juice The culture was carried out at 34° C. and the pH was maintained by buffering the culture medium with MOPS. At the end of the culture, 1,2-propanediol, and residual sucrose, glucose and fructose in the fermentation broth were analysed by HPLC and the yield of 1,2-propanediol over the sum of carbon sources was calculated.

TABLE 3 production of 1,2-propanediol in minimal medium with sugarcane juice as sucrose source.

| Strain/Carbon source | 1,2-propanediol titer (g/l) | 1,2-propanediol yield (g/g carbon source) |
|---|---|---|
| Evolved *E. coli* MG1655 lpd*, ΔtpiA, ΔpflAB, ΔadhE, ΔldhA, ΔgloA, ΔaldA, ΔaldB, Δedd (pUR400)/sugarcane juice | 3.43 +/− 0.22 (n = 2) | 0.15 +/− 0.01 (n = 2) |
| Evolved *E. coli* MG1655 lpd*, ΔtpiA, ΔpflAB, ΔadhE, ΔldhA, ΔgloA, ΔaldA, ΔaldB, Δedd (pKJL101.1)/sugarcane juice | 3.94 +/− 0.94 (n = 3) | 0.26 +/− 0.01 (n = 3) | n is the number of repetitions of the same experiment.
The figures given are the mean and standard deviation of the figures obtained for n repetitions.

Example 4

Production of 1,2-propanediol with Sugarcane Juice Alone or Supplemented with Nutrients The strains obtained as described in Example 1 were cultivated in an Erlenmeyer flask assay under aerobic conditions in a medium containing diluted sugarcane juice (20 g/l sucrose equivalent) either without supplementation or supplemented with phosphate and ammonium (($NH_4$)$_2$$HPO_4$ 2.5 g/l), iron (Fe Citrate, $H_2O$ 0.1 g/l) and thiamine (0.02 g/l).

The culture was carried out at 34° C. and the pH was maintained by buffering the culture medium with MOPS (40 g/l). At the end of the culture, 1,2-propanediol, and residual sucrose, glucose and fructose in the fermentation broth were analysed by HPLC and the yield of 1,2-propanediol over the sum of carbon sources was calculated.

TABLE 4 production of 1,2-propanediol in sugarcane juice without supplementation or in supplemented sugarcane juice.

| Strain/Carbon source | 1,2-propanediol titer (g/l) | 1,2-propanediol yield (g/g carbon source) |
|---|---|---|
| Evolved *E. coli* MG1655 lpd*, ΔtpiA, ΔpflAB, ΔadhE, ΔldhA, ΔgloA, ΔaldA, ΔaldB, Δedd (pUR400)/sugarcane juice | 0.42 (n = 1) | 0.05 (n = 1) |

TABLE 4-continued production of 1,2-propanediol in sugarcane juice without
supplementation or in supplemented sugarcane juice.

| Strain/Carbon source | 1,2-propanediol titer (g/l) | 1,2-propanediol yield (g/g carbon source) |
|---|---|---|
| Evolved *E. coli* MG1655 lpd*, ΔtpiA, ΔpflAB, ΔadhE, ΔldhA, ΔgloA, ΔaldA, ΔaldB, Δedd (pKJL101.1)/sugarcane juice | 1.07 (n = 1) | 0.12 (n = 1) |
| Evolved *E. coli* MG1655 lpd*, ΔtpiA, ΔpflAB, ΔadhE, ΔldhA, ΔgloA, ΔaldA, ΔaldB, Δedd (pUR400)/supplemented sugarcane juice | 2.29 +/− 0.02 (n = 2) | 0.14 +/− 0.00 (n = 2) |
| Evolved *E. coli* MG1655 lpd*, ΔtpiA, ΔpflAB, ΔadhE, ΔldhA, ΔaldA, ΔaldB, Δedd (pKJL101.1)/supplemented sugarcane juice | 4.08 +/− 0.02 (n = 2) | 0.26 +/− 0.00 (n = 2) | n is the number of repetitions of the same experiment.
The figures given are the mean and standard deviation of the figures obtained for n repetitions

REFERENCES (IN THE ORDER OF CITATION IN THE TEXT)

Badia J, Ros J, Aguilar J (1985), *J. Bacteriol.* 161: 435-437
Tran Din K and Gottschalk G (1985), *Arch. Microbiol.* 142: 87-92
Cameron D C and Cooney C L (1986), *Bio/Technology*, 4: 651-654
Sanchez-Rivera F, Cameron D C, Cooney C L (1987), *Biotechnol. Lett.* 9: 449-454
Altaras N E, Etzel M R, Cameron D C (2001), *Biotechnol. Prog.* 17: 52-56
Cameron D C, Altaras N E, Hoffman M L, Shaw A J (1998), *Biotechnol. Frog.* 14: 116-125
Altaras N E and Cameron D C (1999), *Appl. Environ. Microbiol.* 65: 1180-1185
Altaras N E and Cameron D C (2000), *Biotechnol. Prog.* 16: 940-946
Huang K, Rudolph F B, Bennett G N (1999), *Appl. Environ. Microbiol.* 65: 3244-3247
Berrios-Rivera S J, San K Y, Bennett G N (2003), *J. Ind. Microbiol. Biotechnol.* 30: 34-40
Peters D (2006), *Biotechnol. J.* 1: 806-814
Beckers M, Linde R, Danilevich A, Kaminska E, Upite D, Vigants A, Scherbaka R (1999), *Food Biotechnol.* 13: 107-119
Shukla V B, Zhou S, Yomano L P, Shanmugam K T, Preston J F, Ingram L O (2004), *Biotechnol. Lett.* 26: 689-693
Calabia B P and Tokiwa Y (2007), *Biotechnol. Lett.* 29: 1329-1332
Schmid K, Schupfner M, Schmitt R (1982), *J. Bacteriol.* 151: 68-76
Schmid K, Ebner R, Altenbuchner J, Sxhmitt R, Lengeler J W (1988), *Mol. Microbiol.* 2: 1-8
Schmid K, Schupfner M, Schmitt R (1982), *J. Bacteriol.* 151: 68-76
Bockmann J, Heuel H, Lengeler J W (1992), *Mol. Gen. Genet.* 235: 22-32
Jahreis K, Bender L, Bockmann J, Hans S, Meyer A, Siepelmeyer J, Lengeler J W (2002), *J. Bacteriol.* 184: 5307-5316
Tsunekawa H, Azuma S, Okabe M, Okamoto R, Aiba S (1992), *Appl. Environ. Microbiol.* 58 2081-2088
Penfold D W and Macaskie L E (2004), *Biotechnol. Lett.* 26: 1879-1883
Anderson E H (1946), *Proc. Natl. Acad. Sci. USA* 32:120-128
Miller (1992), A Short Course in Bacterial Genetics: A Laboratory Manual and Handbook for *Escherichia coli* and Related Bacteria, Cold Spring Harbor Laboratory Press, Cold Spring Harbor, New York
Schaefer U, Boos W, Takors R, Weuster-Botz D (1999), *Anal. Biochem.* 270: 88-96
Wiesenborn D P, Rudolph R B, Papoutsakis E T (1987), *Appl. Environ. Microbiol.*, 54: 2717-2722
Monot F, Martin J R, Petitdemange H, Gay R (1982), *Appl. Environ. Microbiol.* 44: 1318-1324
Vasconcelos I, Girbal L, Soucaille P (1994), *J. Bacteriol.* 176: 1443-1450

The invention claimed is:

1. A method for producing 1,2-propanediol by fermentation, comprising:
   a) cultivating a strain of *Escherichia coli* producing 1,2-propanediol in a fermentation medium comprising at least a carbon source, and
   b) recovering the 1,2-propanediol being produced, wherein the strain of *Escherichia coli*:
   is genetically modified to comprise a non-phosphotransferase system (non-PTS) sucrose utilization system with the introduction of the genes cscBKAR, wherein the gene cscB codes for a sucrose:proton symport transport system, the gene cscK codes for a fructokinase, the gene cscA codes for an invertase, the gene cscR codes for a sucrose specific receptor, and
   is able to utilize sucrose as a sole carbon source for the production of 1,2-propanediol.

2. The method of claim 1, wherein said fermentation medium comprises at least a source of sucrose as a carbon source.

3. The method of claim 1, wherein said fermentation medium comprises a source of sucrose as a sole carbon source.

4. The method of claim 2 wherein said sucrose source comprises at least 7% of sucrose.

5. The method of claim 3 wherein said sucrose source comprises at least 7% of sucrose.

6. The method of claim 2, wherein said source of sucrose is obtained from biomass.

7. The method of claim 3, wherein said source of sucrose is obtained from biomass.

8. The method of claim 6, wherein said biomass comprises plant biomass.

9. The method of claim 7, wherein said biomass comprises plant biomass.

10. The method of claim 2, wherein said source of sucrose is obtained from a plant selected from sugarcane, sugar beet, sweet sorghum, sugar maple, sugar palm and blue agave.

11. The method of claim 3, wherein said source of sucrose is obtained from a plant selected from sugarcane, sugar beet, sweet sorghum, sugar maple, sugar palm and blue agave.

12. The method of claim 2, wherein said source of sucrose is in the form of juice, concentrated juice or syrup, clarified juice, molasses or crystallized sucrose.

13. The method of claim 3, wherein said source of sucrose is in the form of juice, concentrated juice or syrup, clarified juice, molasses or crystallized sucrose.

14. The method of claim 2, wherein said source of sucrose is a final product, an intermediate product or a by-product of the sugarcane or sugar beet industry.

15. The method of claim 3, wherein said source of sucrose is a final product, an intermediate product or a by-product of the sugarcane or sugar beet industry.

16. The method of claim 1, wherein the fermentation medium contains at least a source of phosphorus and/or a source of nitrogen.

* * * * *